(12) United States Patent
Cheng et al.

(10) Patent No.: US 6,215,032 B1
(45) Date of Patent: Apr. 10, 2001

(54) CATALYST RECOVERY FOR HALOGEN EXCHANGE REACTIONS

(75) Inventors: Chi Hung Cheng; John F. Balhoff; Ronny W. Lin, all of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/021,690

(22) Filed: Feb. 10, 1998

(51) Int. Cl.[7] .............................. C07C 22/00; B01J 31/00
(52) U.S. Cl. ......................... 570/147; 502/162; 502/164
(58) Field of Search .................................. 502/164, 182; 570/147

(56) References Cited

U.S. PATENT DOCUMENTS 5,824,827 * 10/1998 Bildinov et al. ..................... 570/147

OTHER PUBLICATIONS

CAPLUS Abstract of Marchenko et al. "Ammonolysis of triamidohalophosphonium halides", Zh. Obshch. Khim., 1980, vol. 50(3), pp. 679–680.

Koidan et al., "Some Properties of Phosphorimidic Triamides", Translated from Zhurnal Obshchei Khimii, Sep. 1982, vol. 52, No. 9, pp. 1779–1787.

* cited by examiner

Primary Examiner—Alan Siegel
(74) Attorney, Agent, or Firm—Philip M. Pippenger

(57) ABSTRACT

It has been found possible to separate catalytically-active aminophosphonium catalysts from mixtures composed predominately of aminophosphonium catalyst residue(s) and heavy ends from a halogen exchange reaction conducted in an aprotic solvent/diluent by extracting such mixtures with a neutral or acidic aqueous extraction solvent medium. Various ways of isolating from the halogen exchange reaction product mixture a mixture composed predominately of aminophosphonium catalyst residue(s) and heavy ends are described. Halogen exchange processes in which the catalytically-active aminophosphonium catalysts are separated for reuse are also described. Since aminophosphonium catalysts are expensive, the present process technology fulfills a need which has existed for an effective way of recovering such catalysts in catalytically active form enabling reuse of such materials, especially as halogen exchange catalysts.

36 Claims, No Drawings

CATALYST RECOVERY FOR HALOGEN EXCHANGE REACTIONS

TECHNICAL FIELD

This invention relates to halogen exchange reactions involving haloaromatic compounds and alkali metal fluorides, and more particularly to processes for recovering valuable catalyst components for reuse particularly, but not necessarily, in halogen exchange reactions.

BACKGROUND

Halogen exchange reactions for fluorinating haloaromatic compounds using alkali metal fluorides as the fluorine source have been extensively studied heretofore. Typically they involve the reaction of a chloroaromatic compound with potassium fluoride, rubidium fluoride or cesium fluoride by heating the reactants to extremely high temperatures (above about 400° C.) in the absence of an ancillary diluent or solvent, or by conducting the reaction at temperatures of around 200–230° C. in an aprotic solvent such as sulfolane. It has also been reported that organic fluorine compounds such as pentafluorobenzonitrile, tetrafluorophthalonitriles and pentafluoropyridine can be formed by reacting a corresponding chloro- or bromo-substituted compound with alkali metal halide such as potassium fluoride in benzonitrile as solvent at 190° C. to 400° C. in a sealed autoclave under autogenous pressure.

Use of catalysts in some exchange reactions has also been studied. Such catalysts have included quaternary ammonium salts, metal carbonyls, crown ethers and cryptates. In now commonly-owned application Ser. No. 08/754,338, filed Nov. 22, 1996, now U.S. Pat. No. 5,824,827, all disclosure of which is incorporated herein by reference, Igor Bildinov et al. describe a significant improvement in halogen exchange technology, namely that aminophosphonium compounds such as one or more tetra(dihydrocarbylamino) phosphonium halides are highly effective catalysts for halogen exchange reactions whether the reaction is conducted as a mixture of solids or as a slurry.

Aminophosphonium catalysts, such as tetra(dihydrocarbylamino)phosphonium halides, although highly effective as catalysts, are nonetheless relatively expensive materials. Thus it would be highly desirable to recover such catalysts for reuse as catalysts. However, the formation of heavy ends during halogen exchange reactions complicates the recovery of such catalyst components in suitably pure, catalytically active form. Thus a need has existed for an effective way of recovering such catalysts in catalytically active form enabling reuse of such materials, especially as halogen exchange catalysts. This invention is deemed to fulfill this need most expeditiously.

BRIEF SUMMARY OF THE INVENTION

The halogen exchange reactions with which this invention is concerned typically involve heating a mixture formed from ingredients comprising (A) at least one finely-divided alkali metal fluoride, (B) at least one haloaromatic compound having at least one halogen atom of atomic number greater than 9 on an aromatic ring, (C) an aminophosphonium catalyst, and (D) at least one liquid aprotic solvent/diluent at one or more reaction temperatures at which at least one halogen atom of the haloaromatic compound is replaced by a fluorine atom.

In one of its most basic embodiments this invention involves the discovery that it is possible to separate catalytically-active aminophosphonium catalysts from mixtures composed predominately of aminophosphonium catalyst residue(s) and heavy ends from a halogen exchange reaction conducted in an aprotic solvent/diluent. To accomplish this, such mixtures are extracted with a neutral or acidic aqueous extraction solvent medium.

In another of its embodiments this invention provides a process for recovering aminophosphonium catalyst from a halogen exchange reaction mixture in which the reaction was performed using an aminophosphonium catalyst in a liquid aprotic solvent/diluent and in which at least one fluoroaromatic compound was produced and heavy ends were co-produced, which process comprises (i) isolating a liquid mixture composed predominately of aminophosphonium catalyst residue(s) and heavy ends, and (ii) extracting at least a portion of the mixture from (i) with a neutral or acidic aqueous extraction solvent medium to separate aminophosphonium catalyst therefrom.

As regards step (i) above, the liquid mixture composed predominately of aminophosphonium catalyst residue(s) and heavy ends can be isolated in various ways. If volatile materials are not completely withdrawn from the reaction vessel during the reaction, the halogen exchange reaction mixture on completion of the reaction and when at room temperature typically comprises (a) a product which comprises at least one fluorinated aromatic compound, (b) aprotic solvent/diluent, (c) alkali metal halide solids, (d) aminophosphonium catalyst residue(s), and (e) heavy ends. To effect the isolation per step (i) above, at least a portion of the product and at least a portion of the solvent/diluent can be recovered from the reaction vessel and/or reaction mixture by distillation and, if desired, can be separated from each other either during the distillation or by means of a subsequent separation, such as distillation or solvent extraction. The solids can be removed by filtration, centrifugation, or other suitable physical solids-liquid separation procedure, in most cases centrifugation being the preferred method. While the distillation and solids removal can be conducted in any sequence, it is preferred to conduct the solids removal prior to distillation. When these operations have been completed the liquid mixture composed predominately of aminophosphonium catalyst residue(s) and heavy ends remains, usually in the form of an oily residue, and this material is then subjected to extraction step (ii) above.

For conducting the extraction pursuant to this invention, the preferred aqueous extraction media are dilute aqueous hydrochloric acid and dilute aqueous hydrobromic acid. The resulting neutral or acidic aqueous solution of the catalyst which is formed in this process can be heated to remove the water and acid, and thereby provide the catalyst in isolated form. Alternatively, the aqueous solution of the catalyst can be extracted with an organic solvent, preferably an aprotic solvent in which water is substantially insoluble, to provide an organic solution of the catalyst. When the aminophosphonium catalyst is to be recycled in a halogen exchange reaction it is preferable to extract the catalyst from the neutral or acidic aqueous solution of catalyst with a low-boiling organic solvent such as methylene chloride, and then conduct a solvent exchange in which the low-boiling organic solvent is replaced by a higher boiling aprotic solvent such as benzonitrile or nitrobenzene to thereby form a solution of the catalyst in the aprotic solvent. This last mentioned solution is ideally suited for recycle to the halogen exchange reaction.

The use of an aqueous extraction medium makes it possible to separate the aminophosphonium catalyst from both heavy ends and other impurities associated therewith, such as most, if not substantially all, of the residual aprotic solvent entrained in the heavy ends, and at least a portion of catalyst decomposition products such as $KPF_6$ and $(NPF_2)_3$ which are typically contained in the heavy ends. Moreover, the aminophosphonium catalyst can be recovered in suitably purified, catalytically-active form from the neutral or acidic aqueous solution formed in the extraction by use of procedures described herein. Impurities, if any, associated with the recovered aminophosphonium catalyst do not materially detract from the effectiveness of the catalyst when recycled to the same or a subsequent halogen exchange reaction. And in addition, catalyst losses incurred during the catalyst recovery operations when properly conducted pursuant to this invention are well within acceptable limits.

These and other embodiments and features of the invention will become still further apparent from the ensuing description and appended claims.

FURTHER DETAILED DESCRIPTION

Halogen Exchange Reactions

Any aromatic compound that has at least one replaceable halogen atom other than fluorine on the aromatic ring is a candidate ingredient for use in the halogen exchange reaction. The compound may have a homocyclic aromatic nucleus (i.e., at least one benzene ring system) or a heteroaromatic ring system. Also, the compound may contain one or more activating groups such as nitro, nitroso, carbonyl, cyano, sulfonic acid, etc., or it may be devoid of any such group. The compound contains one or more chlorine, bromine or iodine atoms, or any combination of Cl, Br, and/or I atoms on the aromatic ring and may also have one or more such halogen atoms on one or more side chains and/or on one or more non-aromatic homocyclic or heterocyclic rings bonded or fused to the aromatic ring system. In addition the compound may contain one or more fluorine atoms anywhere in the molecule including one or more ar-fluorine atoms provided the compound has at least one aromatic ring that contains at least one replaceable ar-halogen atom other than fluorine. The hetero atom in the halo-substituted aromatic ring where the fluorine substitution is desired is from 1 to 3 nitrogen atoms (e.g., the compound is, or has at least the ring system of, an ar-halopyridine, an ar-halopyridazine, an ar-halopyrimidine, an ar-halopyrazine, an ar-halotriazine where at least one ar-halogen atom is other than a fluorine atom). Other hetero atoms which can be present in side chains or additional ring systems of the compound include one or more nitrogen, oxygen, sulfur, phosphorus, boron or silicon atoms, or combinations of two or more of these. Generally speaking, the haloaromatic ingredient may contain in the range of up to 50 carbon atoms in the molecule, and preferably contains in the range of up to 20 carbon atoms in the molecule.

Preferred are haloaromatic compounds that are devoid of any activating group(s) in the molecule, as these usually undergo a halogen exchange reaction much less readily than their counterparts which have activating functionality in the molecule.

As between the homocyclic and heterocyclic haloaromatics, the homocyclic haloaromatics are preferred ingredients. As noted above, haloaromatics that are devoid of any activating functional group on the aromatic ring to which the halogen atom of atomic number greater than 9 is bonded and in addition, are devoid of any hydrogen atom on that aromatic ring constitute another preferred category of haloaromatic ingredient or feed material for the halogen exchange reaction. Especially preferred haloaromatic compounds of this type are perhaloaromatic compounds of the formula $C_6Cl_nBr_mF_p$ where n is from 0 to 6, m is from 0 to 6 and p is from 0 to 5, and where the sum of n, m and p is 6. Compounds in which m is zero are especially desirable ingredients because of good reactivity in the process and generally lower cost. Moreover, there is a particularly pressing present need for methods for effectively producing polyfluorobenzenes, especially chloropentafluorobenzene and hexafluorobenzene, from suitable perhalobenzene reactants, such as compounds of the formula $C_6F_nX_{6-n}$ where n is 0 to 4, and each X is, independently, a chlorine or bromine atom. Such feeds can be a single compound, or a preformed or pre-existing mixture of two or more compounds of the foregoing formula, or mixture of two or more compounds of the foregoing formula formed in situ in the reactor by use of two or more separate, concurrent or sequential, feeds of one or more such compounds into the reactor. Examples of such feedstocks include hexachlorobenzene, pentachlorofluorobenzene, tetrachlorodifluorobenzene, trichlorotrifluorobenzene, dichlorotetrafluorobenzene, bromopentachlorobenzene, dibromotetrachlorobenzene, tribromotrichlorobenzene, tetrabromodichlorobenzene, pentabromochlorobenzene, hexabromobenzene, pentabromofluorobenzene, tetrabromodifluorobenzene, tribromotrifluorobenzene, dibromotetrafluorobenzene, bromochlorotetrafluorobenzene, dibromochlorotrifluorobenzene, bromodichlorotrifluorobenzene, dibromodichlorodifluorobenzene, bromotrichlorodifluorobenzene tribromochlorodifluorobenzene, bromotetrachlorofluorobenzene, dibromotrichlorofluorobenzene, tribromodichlorofluorobenzene, tetrabromochlorofluorobenzene, and any combination or mixture of any two or more of such compounds. Hexabromobenzene is a preferred feedstock, and hexachlorobenzene is the most preferred feedstock. For convenience, all feedstocks referred to in this paragraph are sometimes referred to hereinafter as perhalobenzene or perhalobenzenes.

Other haloaromatic compounds which can be converted into ar-fluorinated compounds by use of this invention include, for example, mono-, di-, tri-, tetra- and pentachlorobenzenes, and bromo and iodo analogs thereof; mono and polychloro, bromo and iodo naphthalenes, tetrahydronaphthalenes, acenaphthalenes, biphenyls and terphenyls; alkyl- and haloalkyl-substituted analogs of the foregoing; chloro, bromo and iodo diarylethers and monoalkylmonoaryl ethers; 2-chloronitrobenzene; 4-chloronitrobenzene; 2,4-dinitrochlorobenzene; 3,4-dichloronitrobenzene; 3-chloro4-fluoronitrobenzene; 2,4,6-trichloropyrimidine; tetrachloropyrimidine; 2-chlorobenzonitrile; 4-chlorobenzonitrile; pentachlorobenzonitrile; tetrachloroisophthalonitrile; 2-chloropyridine; 2,5-dichloropyridine; pentachloropyridine; 4-chlorophthalic anhydride; and still other similar compounds, such as are referred to in U.S. Pat. No. 4,684,734 to Kaieda, et al.

Potassium fluoride, rubidium fluoride, and cesium fluoride are used as the principal fluorinating agents in the process. Combinations of any two or more of such these alkali metal fluorides can be used. Likewise, mixtures of potassium fluoride, rubidium fluoride and/or cesium fluoride together with sodium fluoride or lithium fluoride, or both, can also be used if desired, although this is not recommended. To enhance its reactivity, the alkali metal fluoride as charged to the reaction mixture is preferably in finely-divided or powdery anhydrous or substantially anhydrous form, i.e., it should not contain, if any, more than about 3000 parts per million (ppm) of water on a weight basis. Potassium fluoride is the preferred fluorinating agent as it is the most cost-effective reagent, and most preferably it will have a water content, if any, below about 1000 ppm. One convenient way of ensuring that the fluorinating agent is suitably anhydrous is to form a slurry of the fluoride salt in a suitable volatile hydrocarbon such as benzene that forms an azeotrope with water, and heat the mixture to dryness, while of course suitably handling and disposing of the vapors. A particularly useful form of alkali metal fluoride for use in the process is may be produced by using the procedure described by T. P. Smyth, A. Carey and B. K. Hodnett in *Tetrahedron*, Volume 51, No. 22, pp. 6363–6376 (1995). In brief, the described procedure involves recrystallizing KF from a methanol solution by slow evaporation of the solvent, followed by drying at 100° C. Another useful form is alkali metal fluoride dispersed on $CaF_2$. See in this connection, J. H. Clark, A. J. Hyde and D. K. Smith, *J. Chem. Soc. Chem. Commun.*, 1986, 791. Other activated forms of alkali metal fluorides such as spray dried (N. Ishikawa, et al. *Chem. Letts.*, 1981, 761), and freeze dried (Y. Kimura, et al. *Tetrahedron Letters*, 1989, 1271) can be used. The four technical papers cited in this paragraph are incorporated in full herein by reference. Ordinarily the alkali metal fluoride particles should have an average surface area of at least about 0.20 $m^2/g$. In this connection, the larger the average surface area of the alkali metal fluoride particles, the better. Thus it is preferred that the alkali metal fluoride initially have an average surface area of at least about 0.40 $m^2/g$, and more preferably at least about 0.80 $m^2/g$. For example, as charged to the reactor in the practice of this invention, spray dried potassium fluoride with a typical water content of about 1000 ppm and an average surface area of about 0.85 $m^2/g$ has been found to give a reaction rate that is approximately four times the rate given under the same conditions by spray dried potassium fluoride with an average surface area of about 0.25 $m^2/g$.

As regards catalyst composition, the material is identified herein as to its composition prior to being combined with any other substance being used in the process. After addition to, and/or mixing with, one or more other components used in the process and/or during the course of the process itself, the catalyst may change in its composition, and if so, the resultant changed material, whatever its makeup and however many changes it may undergo, may be in whole or in part responsible for the functioning of the catalyst. Thus the material is sometimes referred to herein as catalyst or catalyst precursor.

Subject therefore to the foregoing explanation regarding function and composition of the catalyst or catalyst precursor, the materials used for this purpose are aminophosphonium catalysts, more particularly tetra(dihydrocarbylamino)phosphonium halide catalysts. Such compounds can be represented by the formula:

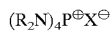

where each R is, independently, a hydrocarbyl group, preferably an alkyl group, and X is a halogen atom, preferably a chlorine or bromine atom. Examples of such aminophosphonium compounds are:

tetrakis(diethylamino)phosphonium fluoride
tetrakis(diethylamino)phosphonium chloride
tetrakis(dipropylamino)phosphonium chloride
tetrakis(dibutylamino)phosphonium chloride
tetrakis(dihexylamino)phosphonium chloride
tetrakis(diphenylamino)phosphonium chloride
tetrakis(di-2-phenethylamino)phosphonium chloride
tris(diethylamino)(dipropylamino)phosphonium chloride
tetrakis(diethylamino)phosphonium bromide
tetrakis(dipropylamino)phosphonium bromide
tetrakis(dibutylamino)phosphonium bromide
tetrakis(dioctylamino)phosphonium bromide
tetrakis(didecylamino)phosphonium bromide
tetrakis(diphenylamino)phosphonium bromide
tetrakis(di-m-tolylamino)phosphonium bromide
tetrakis(dibenzylamino)phosphonium bromide
tetrakis(dicyclohexylamino)phosphonium bromide
tetrakis(diethylamino)phosphonium iodide
tetrakis(dibutylamino)phosphonium iodide.

At present, the most preferred compound is tetrakis(diethylamino)phosphonium bromide. For a method for the preparation of such compounds, see Koidan, Marchenko, Kudryavtsev, and Pinchuk, Zh. *Obshch. Khim.*, 1982, 52, 2001, an English language translation of which is available from Plenum Publishing Corporation.

A procedure which has been used for preparing tetra(diethylamino)phosphonium bromide involves the following four steps (where Et represents an ethyl group):

1) $PCl_3 + 6HN(Et)_2 + CCl_4 \leftrightarrow (Et_2N)_3P^{\oplus}—CCl_3Cl^{\ominus} \leftrightarrow (Et_2N)_3P=CCl_2$
2) $(Et_2N)_3P^{\oplus}—CCl_3Cl^{\ominus} + NH_3 \rightarrow (Et_2N)_3P=NH.HCl + CHCl_3$
3) $(Et_2N)_3P=NH.HCl + NaOH \rightarrow (Et_2N)_3P=NH + NaCl + H_2O$
4) $(Et_2N)_3P=NH + 2NaOH + 2EtBr \rightarrow [(Et_2N)]_4PBr + 2NaBr + 2H_2O$ In this procedure, carbon tetrachloride and phosphorus trichloride are charged to the reactor followed by the slow addition of diethyl amine at low temperature (30° C. maximum). This results in the formation of dichloromethylene phosphoroamidite intermediate. Ammonia (gas) is then charged to the reactor resulting in the formation of an imino hydrochloride phosphoroamidite intermediate. Following a period of stirring, the reactor contents are filtered, and the filtrate is concentrated by evaporation under vacuum. The concentrated filtrate is then treated with sodium hydroxide solution causing the formation of the free base imino phosphoroamidite. This is extracted with dichloromethane. The extracted solution is dried with calcium chloride and the dichloromethane is removed by evaporation. The solid product is mixed with sodium hydroxide and bromoethane is charged. This results in the formation of the product tetra(diethylamino)phosphonium bromide. The product is then extracted with dichloromethane. The extract is dried and the dichloromethane is removed by evaporation. The crude product is then recrystallized from a mixture of dichloromethane and diethyl ether. The recrystallized, wet, product is then dried.

Typical raw materials input for such sequential operations is as follows: carbon tetrachloride, 3985 grams (25.7 moles); phosphorous trichloride, 270 grams (1.96 moles); diethyl amine, 880 grams (12.39 moles); ammonia, 40 grams (2.35 moles); 50% sodium hydroxide, 315 grams; dichloromethane, 472 grams; calcium chloride (anhydrous), 23.6 grams; 20% sodium hydroxide, 534 grams; bromoethane, 230 grams (2.12 moles); dichloromethane, 1643 grams; calcium chloride (anhydrous) 82.1 grams; dichloromethane 450 grams; diethyl ether, and 450 grams. Typically this provides a yield of about 300 grams (0.754 moles) per batch.

The tetra(dihydrocarbylamino)phosphonium halide catalysts are effective when utilized as the only catalyst component charged directly or indirectly (i.e., after admixture with one or more other components being charged to the reaction system. However, the tetra(dihydrocarbylamino) phosphonium halide catalysts can be used in combination with one or more other types of catalysts, provided of course that the benefits provided by the tetra(dihydrocarbylamino) phosphonium halide catalyst are not materially affected adversely by the other catalyst component(s) selected for use. The tetra(dihydrocarbylamino)phosphonium halide catalysts are used in catalytically effective amounts, which typically fall in the range of about 0.01 to about 1 mole per mole of perhalobenzenes in the reaction mixture. Preferred catalytically effective amounts of tetra(dihydrocarbylamino) phosphonium halide catalysts fall in the range of about 0.05 to about 0.3 mole per mole of perhalobenzenes in the reaction mixture.

Other catalysts or catalyst precursors that may be used in combination with the above aminophosphonium catalysts are comprised of one or more crown ethers or crypt compounds. These compounds, sometimes referred to as "cage compounds" may prove helpful in further enhancing the reactivity of the alkali metal fluoride. See in this connection, U.S. Pat. No. 4,174,349 to Evans, et al. A full description of the crown ethers and the crypt compounds is provided by this Evans, et al. patent and references cited therein relating to these materials, namely U.S. Pat. No. 3,687,978; J. J. Christensen, et al., *Chem. Rev.*, 1974, 74, 351; J. S. Bradshaw, et al., *Heterocycl. Chem.*, 1974, 11, 649; C. J. Pedersen, et al., *Angew. Chem. Int. Ed. Engl.*, 1972, 11, 16; the Technical Bulletin of PCR Incorporated entitled KRYPTOFIX; and *J. Org. Chem.*, 1977, Vol 42, No. 10, 2A. The disclosure of each and every one of these documents is incorporated herein in full by reference, and any crown ether or any crypt compound disclosed in any such reference, or for that matter in any prior art publication, can be used. The crown ether or crypt compound is used in a catalytically effective amount, which typically is in the range of about 0.01 to about 1 mole per mole of perhalobenzenes in the reaction mixture.

Another type of catalyst that can be used in combination with the phosphonium catalyst is composed of (i) at least one polyvalent inorganic fluoride of boron, aluminum, tin, phosphorus, titanium, zirconium, hafnium, or silicon, or (ii) at least one a double salt of the polyvalent inorganic fluoride and alkali metal fluoride, or (iii) a combination of (i) and (ii), with the proviso that the inorganic fluoride of (i), (ii) and (iii) is in a stable valency state so that (i), (ii) and (iii), as the case may be, has no oxidizing properties. U.S. Pat. No. 3,453,337 to Bennett, et al., reports that in the uncatalyzed reaction between hexachlorobenzene and KF or NaF, the inclusion of compounds of the types (i), (ii) and (iii) above provides enhanced product yields using milder reaction conditions and shorter reaction times. Examples of suitable polyvalent compounds include $LiBF_4$, $NaBF_4$, $KBF_4$, $K_2SnF_6$, $KPF_6$, $K_2SiF_6$, $Na_2TiF_6$, $K_2TiF_6$, $Na_2ZrF_6$, $K_2ZrF_6$, $Na_2HfF_6$, $K_2HfF_6$, among others. Such compounds can be used in catalytically effective amounts of up to 50% or more of the weight of the alkali metal fluoride charged to the reaction mixture. Typically the amount will fall in the range of about 2 to about 25% of the weight of alkali metal fluoride used.

Combination of all of the above three types of catalysts or catalyst precursors, i.e., the phosphonium halide compounds, the cage compounds, and the polyvalent compounds of the immediately preceding paragraph, can also be used.

In many cases the halogen exchange reaction can be performed under reaction conditions at which a vapor phase is formed and concurrently is removed from the reaction vessel. Thus in embodiments using as feed to the reactor one or more compounds of the formula $C_6F_nCl_{6-n}$, where n is 0, 1, 2, 3, or 4, the reaction conditions used are such as to result in formation of a vapor phase comprising chloropentafluorobenzene and preferably the reaction is performed under conditions such that the weight percentage of chloropentafluorobenzene formed in the process is at least 50 percent of the total perhalobenzenes formed in the process. Thus in these embodiments the process is conducted at one or more temperatures of at least about 160° C. at which a vapor phase comprising chloropentafluorobenzene is formed. Usually it is not necessary to operate at temperatures above about 250° C. to achieve highly desirable reaction rates and high yields of chloropentafluorobenzene. Preferably the reaction is performed at one or more temperatures in the range of about 170 to about 240° C. Particularly preferred temperatures are within the range of about 200° C. to about 240° C., such as for example temperatures of about 210° C. to about 235° C. Temperature gradients within the reaction zone may be utilized.

Similarly in embodiments wherein the feedstock is one or more compounds of the formula $C_6F_nBr_{6-n}$, where n is 0, 1, 2, 3, or 4, the process is conducted at one or more temperatures of at least about 160° C. at which a vapor phase comprising bromopentafluorobenzene is formed and continuously removed. Usually it is not necessary to operate at temperatures above about 250° C. to achieve highly desirable reaction rates and high yields of bromopentafluorobenzene. Preferably the reaction is performed at one or more temperatures in the range of about 170 to about 240° C. Particularly preferred temperatures are within the range of about 200° C. to about 240° C., such as for example temperatures of about 210° C. to about 235° C. Temperature gradients within the reaction zone may be utilized.

When conducting the halogen exchange reaction without recourse to removal of the vapor phase during the reaction, a closed reaction system is typically used. In such cases the temperatures used are usually in the range of about 200 to about 240° C.

In conducting the halogen exchange process, the pressure is a function of the reaction temperature and makeup of the liquid system, especially the solvent, being used. Typically the pressure will fall in the range of about 100 kPa (ca. 15 psia) to about 550 kPa (ca. 80 psia).

The halogen exchange reaction can be carried out as a batch, semi-continuous or continuous process. When feeding or charging into the reactor or reaction zone the components or ingredients used in the process, such substances can be fed or charged continuously or intermittently, or if desired, combinations of continuous and intermittent feeds or charges can be employed. Likewise these substances can be fed or charged individually or in one or more preformed mixtures (e.g., blends and/or solutions), or if desired, one or more of these substances can be fed or charged individually and two or more can be fed or charged in the form of one or more preformed mixtures. In addition, however fed or charged, the feeding or charging can be effected concurrently or sequentially in any order, and if desired, part of the feeding or charging can be effected concurrently and part can be effected sequentially in any order.

Suitable polar aprotic solvents include sulfolane (tetramethylene sulfone), N,N-dimethylformamide, N,N-dimethylacetamide, dimethylsulfone, dimethylsulfoxide, triglyme (triethylene glycol dimethyl ether), benzonitrile, N-methylpyrrolidinone, and like polar aprotic solvents that are in the liquid state at the reaction temperature selected for use, and more preferably that are also in the liquid state at 10° C. or below. Benzonitrile and ring-substituted liquid alkylbenzonitriles (e.g., o-methylbenzonitrile, m-methylbenzonitrile, etc.), and especially benzonitrile itself, are the preferred solvents. Another preferred aprotic solvent is nitrobenzene because of its excellent solvency characteristics and relatively low cost. Liquid ring-substituted alkylmononitrobenzenes are also suitable.

While not critical, it is desirable for most efficient operation to include in the slurry from about 0.05 to about 0.3 mole of the tetra(dihydrocarbylamino)phosphonium halide per mole of perhalobenzene being used in forming the slurry. The reaction of the alkali metal fluoride with the perhalobenzene reactant involves one molecule of the alkali metal fluoride per atom of non-fluoro-halogen to be replaced on the perhalobenzene by a fluorine atom, and thus the slurry should be formed from an amount of alkali metal fluoride equivalent to at least one molecule of alkali metal fluoride per atom of such nonfluoro-halogen to be replaced. An excess of up to about 3 moles of alkali metal fluoride per atom of replaceable halogen atoms can be used, especially when it is desired to force the reaction toward complete or substantially complete replacement of each replaceable non-fluoro-halogen atom of the perhalobenzene reactant. The amount of the polar aprotic solvent(s) used in forming the slurry will typically be proportioned to provide a slurry in which the solids content is the range of about 5 to about 35 percent by weight. In order to achieve the highest reaction rates without excessive energy requirements for stirring or otherwise agitating the slurry, the solids content of the slurry is preferably kept in the range of about 20 to about 30 percent by weight.

Reaction times or reaction periods within the reaction zone will typically fall in the range of about 3 to about 24 hours (preferably about 3 to about 12 hours), and as a general rule the higher the reaction temperature, the shorter the reaction time.

The reaction mixture should be anhydrous or substantially anhydrous before reaching the temperature at which the halogen exchange reaction is initiated, and preferably the reaction mixture should be anhydrous or substantially anhydrous ab initio. The term "substantially anhydrous" as used in this document with reference to the reaction mixture, i.e., the mixture of the reactants, catalyst(s), and solvent(s), means that the total water content of the mixture at the commencement of the exchange reaction at about 160° C. or above is below about 2000 ppm (wt/wt) and preferably below about 1500 ppm. In general, the lower the water content, the better. Excessive water can kill the reaction. Therefore it is desirable not only to use anhydrous or substantially anhydrous alkali metal fluoride (not more than about 3000 ppm, as noted above), but to ensure that the other components being used are sufficiently dry (i.e., have water contents, if any, that are sufficiently low as to keep the total water content of the overall mixture below about 2000 ppm (wt/wt) and preferably below about 1500 ppm. For example, if industrial grades of polar aprotic solvents contain excessive amounts of water, it is desirable to dry the solvent to a level of, say, 100 ppm, preferably down to a level of about 50 ppm (wt/wt) by means of azeotropic distillation or use of molecular sieves. It is usually very difficult to produce, maintain and use chemicals, especially in a large scale chemical facility, in an absolutely anhydrous condition. Thus the term "anhydrous" is used herein in the same sense as those skilled in the art understand the term. Thus, if by chance the substance used has absolutely zero water content, it is, of course "anhydrous". But even if it does not have zero water content, as long as the water content is in the trace range so that the effect of the water present is of no material consequence and the water content complies with manufacturer's specifications and/or designations of "anhydrous", the substance is deemed herein to be "anhydrous". Without limiting the generality of the foregoing, one commercial supplier, Aldrich Chemical Company, in its 1996–1997 Catalog Handbook of Fine Chemicals refers to a group of listed "anhydrous solvents" on page 1773 thereof as having a water content of <0.005%. Other suppliers may specify other maximum water contents for their "anhydrous" grades, so there is no exact fine line of distinction between "anhydrous" and "substantially anhydrous".

Step (i)—Isolating a Liquid Mixture Composed Predominately of Aminophosphonium Catalyst Residue(s) and Heavy Ends As noted above, a liquid mixture composed predominately (more than 50% by weight) of aminophosphonium catalyst residue(s) and heavy ends can be isolated from the halogen exchange reaction mixture in various ways. If volatile materials are not withdrawn from the reaction vessel during the halogen exchange reaction, the halogen exchange reaction mixture on completion of the reaction and when at room temperature typically comprises (a) a product which comprises at least one fluorinated aromatic compound, (b) aprotic solvent/diluent, (c) alkali metal halide solids, (d) aminophosphonium catalyst residue(s), and (e) heavy ends.

The heavy ends are oily-like materials which do not boil when heated at least as high as 210° C. at atmospheric pressure, and in most cases the heavy ends can be heated at least as high as 230° C. at atmospheric pressure without boiling taking place.

To effect the isolation per step (i), the product (a) and at least a portion of the solvent/diluent (b) can be recovered and concurrently or subsequently separated from each other by distillation. The boiling temperatures of the particular fluoroaromatic reaction product(s) formed and of the particular aprotic solvent(s) used will of course be taken into consideration when selecting the temperature and pressure conditions to be used for such distillation, and such matters are well within the skill of any chemist or chemical engineer. The solids (c) can be removed by filtration, centrifugation, or other suitable physical solids-liquid separation procedure. In most cases centrifugation is the preferred method. Here again, the conditions used for this physical separation can readily be determined in any given case by those of skill in the art. While the distillation and the solids removal can be conducted in any sequence, it is preferred to conduct the solids removal prior to distillation. When these operations have been completed, the liquid mixture composed predominately of aminophosphonium catalyst residue(s) and heavy ends remains, usually in the form of an oily residue. Smaller amounts of other materials such as residual fluoroaromatic product or intermediates and/or by-products formed during the reaction and/or organic impurities can be present, although it is desirable to minimize the amount of such materials in this mixture. Whatever its makeup, this mixture is then subjected to step (ii).

Step (ii—Extracting Mixture from Step (i) with a Neutral or Acidic Aqueous Extraction Solvent Medium to Separate Aminophosphonium Catalyst Therefrom An aqueous medium is used for conducting this extraction. While pure water or a dilute aqueous saline solution can be used in conducting step (ii), the preferred aqueous extraction media are dilute aqueous hydrochloric acid (e.g., ca. 0.5 to ca. 5 wt % HCl) and dilute aqueous hydrobromic acid (e.g., ca. 0.5 to ca. 5 wt % HBr). The particular manner by which the extraction is carried out is not critical, and any of a number of various extraction procedures can be used. In any case the extraction operation is typically conducted in such a way as to ensure intimate contact between the aqueous solvent medium and the liquid mixture containing the aminophosphonium catalyst residue(s) and heavy ends. Depending upon the amount and viscosity of the heavy ends present, it may prove advantageous to conduct the extraction operation at an elevated temperature, e.g., ca. 30 to ca. 60° C. However, operation at room temperatures can be used whenever deemed appropriate under the particular circumstances at hand.

The resulting extract, typically a neutral or acidic aqueous solution of the aminophosphonium catalyst, can be subjected to various additional workup procedures. For example, the aqueous extract can be heated to remove the water (and acid if used), and thereby provide the catalyst in isolated form. If desired, the isolated catalyst can be subjected to crystallization to remove impurities. Another way of working up the aqueous extract is to extract this solution with an aprotic organic solvent of the type described hereinabove, preferably one in which water is insoluble or substantially insoluble. If the organic solvent used dissolves a larger amount of water, it may be necessary to dry the resultant "wet" organic solution in a conventional manner, so that the solution is substantially anhydrous before using the organic solution of aminophosphonium catalyst as feed to a halogen exchange reaction.

When the aminophosphonium catalyst is to be recycled in a halogen exchange reaction it is preferable to extract the catalyst from the neutral or acidic aqueous solution of catalyst with a low-boiling organic solvent such as methylene chloride, and then conduct a solvent exchange in which the low-boiling organic solvent is replaced by a higher boiling aprotic solvent such as benzonitrile or nitrobenzene to thereby form a solution of the catalyst in the aprotic solvent. This replacement can be effected by boiling off the initial organic solvent and then adding the aprotic solvent. However, use of a solvent exchange or "solvent-swap" procedure is preferable in plant sized facilities. In a "solvent-swap" procedure the aprotic solvent is gradually added to the mixture to replace the low boiling organic solvent as it is being distilled off and collected.

The solution of the aminophosphonium catalyst in anhydrous or substantially anhydrous aprotic solvent such as sulfolane, benzonitrile or nitrobenzene is ideally suited for recycle to the halogen exchange reaction.

The following Examples are presented for purposes of illustration and not limitation. Examples 1–4 illustrate the recovery and recycle of aminophosphonium catalyst in a series of consecutive batch processes.

EXAMPLE 1

Using all Fresh Raw Materials

A. HALOGEN EXCHANGE REACTION. A 1-liter stainless steel pressure reactor was charged with 12.0 g of tetra(diethylamino)phosphonium bromide (about 95% purity, 28.5 mmole)), 115 g of hexachlorobenzene, 164 g of potassium fluoride having an average surface area of about 0.33 m$^2$/g (LaPorte Industries, Ltd.), and 500 g of nitrobenzene. The reactor was heated to 220° C. After 10.5 hours and the pressure had reached 24 psig, the reactor was vented to about 1 psig through an air-cooled condenser. Distillate (P1) (106.8 g) was collected and was analyzed by gas-chromatography, and was found to contain 19.4 wt % of hexafluorobenzene (F6), 23.0 wt % of chloropentafluorobenzene (F5), 8.2 wt % of dichlorotetrafluorobenzene (F4), 1.3 wt % of trichlorotrifluorobenzene (F3), and 48.1 wt % of nitrobenzene. Distillate PI contained a substantial portion of the fluorinated aromatic compounds produced in the halogen exchange reaction.

B. CENTRIFUGATION. After cooling, the above reaction mass was centrifuged. The solid was washed with 83.1 g of nitrobenzene and the final weight of the solid was 222 g. The centrate was then evaporated using a rotary evaporator with the final condition of 107° C. and 10 mm Hg absolute. The distillate (P2) was analyzed by gas-chromatography. The yields of F6, F5, F4, and F3, which were calculated based on the hexachlorobenzene charged and the products P1 and P2 combined, were 27.8%, 33.7%, 18.2%, and 6.2%, respectively.

C. EXTRACTION. The residual oil-like materials in the bottom flask (25.1 g) were then washed with 63.0 g 2% HCl. The heavy layer (19.7 g) was analyzed by P-NMR to contain 6.2 mmole catalyst (22% of the original catalyst) and other phosphorus compounds. The aqueous material was then extracted twice with methylene chloride, $CH_2Cl_2$, (52.1 g and 72.0 g).

D. SOLVENT EXCHANGE. 15% Caustic (NaOH) (0.21 g) was first added to neutralize the catalyst/$CH_2Cl_2$ solution. The solution was then evaporated to remove most of the $CH_2Cl_2$, nitrobenzene was added, and the resultant solution was evaporated again until all the water was removed. The final solution (26.65 g) of catalyst in nitrobenzene was analyzed by NMR and was found to contain 14.9 mmole catalyst (52% of the original catalyst).

EXAMPLE 2

1st Catalyst and Solvent Recycle

A. HALOGEN EXCHANGE REACTION. A 1-liter stainless steel pressure reactor was charged with 25.4 g of the recovered nitrobenzene solution of catalyst (14.2 mmole catalyst) from Example 1, 6.34 g of fresh tetra(diethylamino)phosphonium bromide (about 95% purity, 15.9 mmole), 105 g of hexachlorobenzene (368.7 mmole), 164 g of potassium fluoride having an average surface area of about 0.33 m$^2$/g (LaPorte Industries, Ltd.), and 471 g of recycle solvent (P2 from Example 1, 96.5 wt % nitrobenzene, 0.06 wt % F6, 0.62 wt % F5, 1.46 wt % F4, 0.89 wt % F3). The reactor was heated to 220° C. After 7 hours and the pressure had reached 28 psig, the reactor was vented to about 1 psig through an air-cooled condenser. Distillate (P1) (91.8 g) was collected and was analyzed by gas-chromatography and was found to contain 21.7 wt % F6, 26.5 wt % F5, 9.5 wt % F4, 1.6 wt % F3, and 41.6 wt % nitrobenzene. Distillate P1 contained a substantial portion of the fluorinated aromatic compounds produced in the halogen exchange reaction.

B. CENTRIFUGATION. After cooling, the reaction mass was centrifuged. The solid was washed with 132.5 g of nitrobenzene and the final weight of the solid was 204 g. The centrate was then evaporated using a rotary evaporator with the final condition of 110° C. and 5 mm Hg absolute. The distillate (P2) was analyzed by gas-chromatography. The yields of F6, F5, F4, and F3, which were calculated based on the fresh and recycle aromatics charged and the products P1 and P2 combined, were 24.9%, 34.5%, 20.5%, and 7.8%, respectively.

C. EXTRACTION. The residual oil-like materials in the bottom flask (27.6 g) were then washed twice with 2% HCl (35.4 g and 30.0 g). The heavy layer (15.3 g) was analyzed by P-NMR and was found to contain 5.3 mmole catalyst (17% of the original catalyst) and other phosphorous compounds. The aqueous material was then extracted twice with methylene chloride (46.3 g and 48.6 g).

D. SOLVENT EXCHANGE. 15% Caustic (0.25 g) was first added to neutralize the catalyst/$CH_2Cl_2$ solution. The solution was then evaporated to remove most of the $CH_2Cl_2$, nitrobenzene was added, and the resultant solution was evaporated until all the water was removed. The final solution (42.6 g) of catalyst in nitrobenzene was analyzed by NMR to contain 19.8 mmole catalyst (66% of the original catalyst).

EXAMPLE 3

2nd Catalyst and Solvent Recycle

A. HALOGEN EXCHANGE REACTION. A 1-liter stainless steel pressure reactor was charged with 41.7 g of the recovered nitrobenzene solution of catalyst (19.4 mmole of catalyst) from Example 2, 4.2 g of fresh tetra(diethylamino) phosphonium bromide (about 95% purity, 10.5 mmole), 110 g of hexachlorobenzene (386 mmole), 164 g of potassium fluoride having an average surface area of about 0.33 $m^2/g$ (LaPorte Industries, Ltd.), and 468 g of recycle solvent (P2 from Example 2, 95.0 wt % nitrobenzene, 1.01 wt % F5, 1.89 wt % F4, 1.14 wt % F3). The reactor was heated to 220° C. After 8 hours and the pressure reached 30 psig, the reactor was vented to about 1 psig through an air-cooled condenser. Distillate (P1) (86.4 g) was collected and was analyzed by gaschromatography and was found to contain 24.0 wt % F6, 29.2 wt % F5, 9.8 wt % F4, 1.6 wt % F3, and 36.2 wt % nitrobenzene. Distillate P1 contained a substantial portion of the fluorinated aromatic compounds produced in the halogen exchange reaction.

B. CENTRIFUGATION. After cooling, the reaction mass was centrifuged. The solid was washed with 145 g of nitrobenzene and the final weight of the solid was 225 g. The centrate was then evaporated using a rotary evaporator with the final condition of 100° C. and 14 mm Hg absolute. The distillate (P2) was analyzed by gas-chromatography. The yields of F6, F5, F4, and F3, which were calculated based on the fresh and recycle aromatics charged and the products P1 and P2 combined, were 23.9%, 34.4%, 21.3%, and 8.2%, respectively.

C. EXTRACTION. The residual oil-like materials in the bottom flask (23.8 g) were then washed twice with 4% HCl (32.8 g and 36.7 g). The heavy layer (16.7 g) was analyzed by P-NMR and was found to contain 5.0 mmole of catalyst (17% of the original catalyst) and other phosphorous compounds. The aqueous material was then extracted twice with methylene chloride (47.5 g and 50.2 g).

D. SOLVENT EXCHANGE. 15% Caustic (0.25 g) was first added to neutralize the catalyst/$CH_2Cl_2$ solution. The solution was then evaporated to remove most of the $CH_2Cl_2$, nitrobenzene was added, and the resultant solution was evaporated until all the water was removed. The final solution (25.3 g) of catalyst in nitrobenzene was analyzed by NMR and was found to contain 17.2 mmole catalyst (57% of the original catalyst).

EXAMPLE 4

3rd Catalyst and Solvent Recycle.)

A. HALOGEN EXCHANGE REACTION. A 1-liter stainless steel pressure reactor was charged with 25.1 g the recovered nitrobenzene solution of catalyst (17.0 mmole of catalyst) from Example 3, 5.2 g of fresh tetra(diethylamino) phosphonium bromide (about 95% purity, 13.0 mmole), 110 g of hexachlorobenzene (386 mmole), 164 g of potassium fluoride having an average surface area of about 0.33 $m^2/g$ (LaPorte Industries, Ltd.), and 482 g of recycle solvent (P2 from Example 3, 94.4 wt % nitrobenzene, 1.27 wt % F5, 2.3 wt % F4, 1.3 wt % F3). The reactor was heated to 220° C. After 8 hours and the pressure had reached 30 psig, the reactor was vented to about 1 psig through an air-cooled condenser. Distillate (P1) (63.5 g) was collected and was analyzed by gaschromatography and was found to contain 33.3 wt % F6, 32.2 wt % F5, 8.5 wt % F4, 1.1 wt % F3, and 26.1 wt % nitrobenzene. Distillate P1 contained a substantial portion of the fluorinated aromatic compounds produced in the halogen exchange reaction.

B. CENTRIFUGATION. After cooling, the reaction mass was centrifuged. The solid was washed with 125 g of nitrobenzene and the final weight of the solid was 210 g. The centrate was then evaporated using a rotary evaporator with the final condition of 106° C. and 5 mm Hg absolute. The distillate (P2) was analyzed by gas-chromatography. The yields of F6, F5, F4, and F3, which were calculated based on the fresh and recycle aromatics charged and the products P1 and P2 combined, were 25.7%, 35.5%, 20.0%, and 7.2%, respectively.

EXAMPLE 5

Using Only Water for Catalyst Extraction

A. HALOGEN EXCHANGE REACTION. A 1-liter stainless steel pressure agitated reactor was charged with 12.0 g of tetra(diethylamino)phosphonium bromide (about 95% purity, 28.5 mmole), 115 g of hexachlorobenzene, 164 g of potassium fluoride having an average surface area of about 0.85 $m^2/g$ (Mitsuya Boeki Ltd.), and 420 g of benzonitrile. The reactor was heated by a concentric electrically heated furnace. All the inerts were removed from the reactor by venting to atmospheric pressure when the temperature reached 200° C. The reaction temperature was ramped to 220° C. within 30 minutes after venting. After 5.5 hours at 220° C. and the pressure had reached 30 psig, the reactor was vented to about 8 psig through an air-cooled condenser. Distillate (P1) (70.8 g) was collected and was analyzed by gas-chromatography. The analysis indicated that it contained 22.4 wt % of hexafluorobenzene (F6), 26.2 wt % of chloropentafluorobenzene (F5), 7.0 wt % of dichlorotetrafluorobenzene (F4), 1.1 wt % of trichlorotrifluorobenzene (F3), and 43.3 wt % of benzonitrile. Distillate P1 contained a substantial portion of the fluorinated aromatic compounds produced in the halogen exchange reaction.

B. CENTRIFUGATION AND EVAPORATION. After cooling, the remaining reaction slurry was centrifuged. The solid was washed with 94 g of benzonitrile and the final weight of the solid was 225 g. The centrate was then evaporated using a rotary evaporator with the final condition of 1 10° C. and 15 mm Hg absolute. The distillate (P2) was analyzed by gas-chromatography. The yields of F6, F5, F4, and F3, which were calculated based on the hexachlorobenzene charged and the products P1 and P2, were 23.0%, 37.3%, 18.2%, and 7.3%, respectively.

C. EXTRACTION. The residual oil-like materials in the bottom flask (17.6 g) were then washed twice with water (77.56 g and 67.32 g). The heavy layer (10.1 g) was analyzed by P-NMR and was found to contain 6.3 mmole of catalyst (22% of the original catalyst) and other phosphorous compounds. The combined aqueous materials were then evaporated almost to dryness and then benzonitrile (38.5 g) was added and then evaporated was resumed until all the water was removed. The final solution (19.6 g) of catalyst in benzonitrile was analyzed by P-NMR and was found to contain 14.2 mmole of catalyst (50% of the original catalyst) and to contain no other phosphorus compounds which were present in the heavy layer.

EXAMPLE 6

Using Two Water Extractions and One HCl Extraction

A. HALOGEN EXCHANGE REACTION. A 1-liter reactor was charged with 12.0 g of tetra(diethylamino)phosphonium bromide (about 95% purity, 28.5 mmole)), 115 g of hexachlorobenzene, 164 g of potassium fluoride having an average surface area of about 0.85 m$^2$/g (Mitsuya Boeki Ltd.), and 420 g of benzonitrile. The reactor was heated to 220° C. in the same manner as in Example 5. After 5 hours at 220° C. and the pressure had reached 30 psig, the whole reaction content was cooled to about 25° C.

B. CENTRIFUGATION AND EVAPORATION. After cooling, the reaction mass was centrifuged. The solid was washed with 74 g of benzonitrile and the final weight of the solid was 227 g. The centrate was then evaporated using a rotary evaporator with the final condition of 107° C. and 15 mm Hg absolute. The distillate was analyzed by gaschromatography. The yields of F6, F5, F4, and F3, which were calculated based on the hexachlorobenzene charged, were 17.0%, 35.2%, 20.4%, and 8.2%, respectively. This distillate contained a substantial portion of the fluorinated aromatic compounds produced in the halogen exchange reaction.

C. EXTRACTION. The residual oil-like materials in the bottom flask (20.8 g) were then washed twice with water (34.7 g and 46.3 g) and once with 1.8% hydrochloric acid (28.7 g). The heavy layer (11.0 g) was analyzed by P-NMR and was found to contain 2.2 mmole of catalyst (8% of the original catalyst) and other phosphorous compounds. The combined aqueous materials were then evaporated almost to dryness and then benzonitrile (37.1 g) was added and evaporated was resumed until all the water was removed. The final solution (29.9 g) of catalyst in benzonitrile was analyzed by P-NMR and was found to contain 21.5 mmole catalyst (75% of the original catalyst) and to contain no other phosphorous compounds which were present in the heavy layer.

EXAMPLE 7

Using Two HCl Extractions

A. HALOGEN EXCHANGE REACTION. A 1-liter stainless steel pressure agitated reactor was charged with 12.0 g of tetra(diethylamino)phosphonium bromide (about 95% purity, 28.5 mmole), 115 g of hexachlorobenzene, 164 g of potassium fluoride having an average surface area of about 0.85 m$^2$/g (Mitsuya Boeki Ltd.), and 420 g of benzonitrile. The reactor was heated to 220° C. in the same manner as in Example 5. After 5.5 hours at 220° C. and the pressure had reached 30 psig, the reactor was vented to about 8 psig through an air-cooled condenser. Distillate (P1) (81.8 g) was collected and was analyzed by gas-chromatography and was found to contain 18.9 wt % F6, 24.7 wt % F5, 7.4 wt % F4, 1.2 wt % F3, and 47.8 wt % benzonitrile. Distillate P1 contained a substantial portion of the fluorinated aromatic compounds produced in the halogen exchange reaction.

B. CENTRIFUGATION. After cooling, the reaction mass was centrifuged. The solid was washed with 85 g of benzonitrile and the final weight of the solid was 217 g. The centrate was then evaporated using a rotary evaporator with the final condition of 108° C. and 14 mm Hg absolute. The distillate (P2) was analyzed by gas-chromatography. The yields of F6, F5, F4, and F3, which were calculated based on the hexachlorobenzene charged and the products P1 and P2 combined, were 22.6%, 38.4%, 20.6%, and 8.1%, respectively.

C. EXTRACTION. The residual oil-like materials in the bottom flask (18.7 g) were then washed twice with 2% hydrochloric acid (28.8 g and 36.3 g). The heavy layer (11.1 g) was analyzed by P-NMR and was found to contain 2.7 mmole catalyst (9.4% of the original catalyst) and other phosphorous compounds. The combined aqueous materials were then evaporated almost to dryness and then benzonitrile (43.9 g) was added and evaporation was resumed until all the water was removed. The final solution (35.2 g) of catalyst in benzonitrile was analyzed by P-NMR and was found to contain 21 mmole of catalyst (75% of the original catalyst) and to contain no other phosphorus compounds which were present in the heavy layer.

EXAMPLE 8

Using Two HBr Extractions

A. HALOGENEXCHANGE REACTION. A 1-liter stainless steel pressure agitated reactor was charged with 12.0 g of tetra(diethylamino)phosphonium bromide (about 95% purity, 28.5 mmole), 115 g of hexachlorobenzene, 164 g of potassium fluoride having an average surface area of about 0.85 m$^2$/g (Mitsuya Boeki Ltd.), and 420 g of benzonitrile. The reactor was heated to 220° C. in the same manner as in Example 5. After 5.5 hours at 220° C. and the pressure had reached 30 psig, the reactor was vented to about 8 psig through an air-cooled condenser. Distillate (P1) (78.7 g) was collected and was analyzed by gas-chromatography and was found to contain 21.3 wt % F6, 24.6% F5, 6.6 wt % F3, and 46.4 wt % benzonitrile. Distillate P1 contained a substantial portion of the fluorinated aromatic compounds produced in the halogen exchange reaction.

B. CENTRIFUGATION. After cooling, the reaction mass was centrifuged. The solid was washed with 76 g of benzonitrile and the final weight of the solid was 221 g. The centrate was then evaporated using a rotary evaporator with the final condition of 1 10° C. and 15 mm Hg absolute. The distillate (P2) was analyzed by gas-chromatography. The yields of F6, F5, F4, and F3, which were calculated based on the hexachlorobenzene charged and the products P1 and P2 combined, were 24.4%, 37.8%, 19.4%, and 7.4%, respectively.

C. EXTRACTION. The residual oil-like materials in the bottom flask (18.7 g) were washed twice with 5.5% hydrobromic acid (35.5 g and 24.1 g). The heavy layer (12.1 g) was analyzed by P-NMR and was found to contain 4.1 mmole of catalyst (15% of the original catalyst) and other phosphorus compounds. The combined aqueous materials were then evaporated almost to dryness and then benzonitrile (48.5 g) was added and evaporation was resumed until all the water was removed. The final solution (30.5 g) of catalyst in benzonitrile was analyzed by P-NMR and was found to contain 18.7 mmole of catalyst (66% of the original catalyst) but no other phosphorus compounds that were present in the heavy layer.

EXAMPLE 9

Using Recycle Catalyst for Reaction

A. HALOGEN EXCHANGE REACTION. A 1-liter stainless steel pressure agitated reactor was charged with 16.0 g of recovered catalyst in benzonitrile solution (11.5 mmole catalyst) from Example 6 and 30.3 g of recovered catalyst in benzonitrile solution (18.1 mmole catalyst) from Example 7, 115 g of hexachlorobenzene, 164 g of potassium fluoride having an average surface area of about 0.85 m$^2$/g (Mitsuya Boeki Ltd.), and 388 g of benzonitrile. The reactor was heated to 220° C. in the same manner as in Example 5. After 5.3 hours at 220° C. and the pressure had reached 30 psig, the reactor was vented to about 8 psig through an air-cooled condenser. Distillate (P1) (103 g) was collected and was analyzed by gas-chromatography and was found to contain 17.0 wt % F6, 23.5 wt % F5, 7.1 wt % F4, 1.2 wt % F3, and 51.2 wt % benzonitrile. Distillate P1 contained a substantial portion of the fluorinated aromatic compounds produced in the halogen exchange reaction.

B. CENTRIFUGATION. After cooling, the reaction mass was centrifuged. The solid was washed with 79 g of benzonitrile and the final weight of the solid was 225 g. The centrate was then evaporated using a rotary evaporator with the final condition of 110° C. and 13 mm Hg absolute. The distillate (P2) was analyzed by gas-chromatography. The yields of F6, F5, F4, and F3, which were calculated based on the hexachlorobenzene charged and the products P1 and P2 combined, were 24.7%, 40.2%, 19.1%, and 7.2%, respectively.

C. EXTRACTION. The residual oil-like materials in the bottom flask (15.8 g) were then washed twice with hydrochloric acid (1.7%, 35.6 g and 3.8%, 23.3 g). The heavy layer (9.3 g) was analyzed by P-NMR and was found to contain 1.6 mmole catalyst (6.3 of the original catalyst) and other phosphorus compounds. The combined aqueous materials were then evaporated almost to dryness and then benzonitrile (44.1 g) was added and evaporation was resumed until all the water was removed. The final solution (22.2 g) of catalyst in benzonitrile was analyzed by P-NMR and was found to contain 20 mmole of catalyst (78% of the original catalyst) and to contain no other phosphorus compounds which were present in the heavy layer.

It can be seen from the above that the aminophosphonium catalyst recovered in the practice of this invention can be quite pure or it can be in admixture with small quantities (e.g., less than about 5 wt %) of other phosphorus-containing or other impurities. Thus throughout this disclosure and in the appended claims when referring to the recovered catalytic material, the term "aminophosphonium catalyst" means and is intended to mean and encompass both (i) pure aminophosphonium catalyst and (ii) aminophosphonium catalyst containing impurities which remain associated therewith when conducting the recovery process pursuant to this invention, provided the amount of such impurities is insufficient to destroy the catalytic activity of the recovered material in a halogen exchange reaction performed as described herein.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of separating a catalytically-active aminophosphonium catalyst from a mixture composed predominately of aminophosphonium catalyst residue(s) and heavy ends from a halogen exchange reaction conducted using an aminophosphonium catalyst in an aprotic solvent/diluent, said process comprising extracting said mixture with a neutral or acidic aqueous extraction solvent medium to form a neutral or acidic aqueous extract, and then separating aminophosphonium catalyst from the aqueous extract.

2. A process according to claim 1 wherein said aqueous extraction solvent medium consists essentially of water.

3. A process according to claim 1 wherein said aqueous extraction solvent medium consists essentially of dilute hydrochloric acid.

4. A process according to claim 1 wherein said aqueous extraction solvent medium consists essentially of dilute hydrobromic acid.

5. A process according to claim 1 further comprising recycling at least a portion of the separated aminophosphonium catalyst to the same or a subsequent halogen exchange reaction.

6. A process according to claim 1 further comprising boiling off the aqueous medium from said aqueous extract.

7. A process according to claim 1 further comprising separating aminophosphonium catalyst from said aqueous extract by distilling off the water as an azeotrope with an organic solvent that forms an azeotrope with water.

8. A process according to claim 1 further comprising extracting aminophosphonium catalyst from said aqueous extract with an organic solvent to form a solution of aminophosphonium catalyst in said organic solvent.

9. A process according to claim 8 wherein said organic solvent is an aprotic solvent.

10. A process according to claim 8 wherein said organic solvent is sulfolane, benzonitrile or nitrobenzene.

11. A process according to claim 1 further comprising extracting aminophosphonium catalyst from said aqueous extract with a first organic solvent and then replacing said first organic solvent with a second solvent which is an aprotic solvent having a higher boiling temperature than said first solvent.

12. A process according to claim 11 wherein said first organic solvent is methylene chloride and said second solvent is sulfolane, benzonitrile or nitrobenzene.

13. A process according to claim 1 further comprising (a) extracting aminophosphonium catalyst from said aqueous extract with a first organic solvent, (b) replacing said first organic solvent with a second solvent which is an aprotic solvent having a higher boiling temperature than said first solvent to form a catalyst solution, and (c) recycling at least a portion of the catalyst solution to the same or a subsequent halogen exchange reaction.

14. A process according to claim 13 wherein said first organic solvent is methylene chloride and said second solvent is benzonitrile or nitrobenzene.

15. A process according to any of claims 1–14 wherein the aminophosphonium catalyst consists essentially of tetra (diethylamino)phosphonium bromide or tetra(diethylamino) phosphonium chloride.

16. A process for recovering aminophosphonium catalyst from a halogen exchange reaction mixture wherein the reaction is performed using an aminophosphonium catalyst in a liquid aprotic solvent/diluent, and wherein the reaction produces a fluoroaromatic compound and co-produces heavy ends, said process comprising (i) isolating a liquid mixture composed predominately of aminophosphonium catalyst residue(s) and heavy ends, (ii) extracting at least a portion of the mixture from (i) with a neutral or acidic aqueous extraction solvent medium to form an aqueous extract containing aminophosphonium catalyst.

17. A process according to claim 16 wherein said aqueous extraction solvent medium consists essentially of water.

18. A process according to claim 16 wherein said aqueous extraction solvent medium consists essentially of dilute hydrochloric acid.

19. A process according to claim 16 wherein said aqueous extraction solvent medium consists essentially of dilute hydrobromic acid.

20. A process according to claim 16 further comprising (iii) separating aminophosphonium catalyst from the aqueous extract.

21. A process according to claim 20 further comprising recycling at least a portion of the separated aminophosphonium catalyst to the same or a subsequent halogen exchange reaction.

22. A process according to claim 20 wherein the aminophosphonium catalyst is separated from the aqueous extract by boiling off the aqueous medium from said aqueous extract.

23. A process according to claim 20 wherein the aminophosphonium catalyst is separated from the aqueous extract by extracting aminophosphonium catalyst from said aqueous extract with an organic solvent to form a solution of aminophosphonium catalyst in said organic solvent, and optionally drying said last-mentioned solution.

24. A process according to claim 23 wherein said organic solvent is an aprotic solvent.

25. A process according to claim 23 wherein said organic solvent is sulfolane, benzonitrile or nitrobenzene.

26. A process according to claim 20 wherein the aminophosphonium catalyst is separated from the aqueous extract by extracting aminophosphonium catalyst from said aqueous extract with a first organic solvent and then replacing said first organic solvent with a second solvent which is an aprotic solvent having a higher boiling temperature than said first solvent.

27. A process according to claim 26 wherein said first organic solvent is methylene chloride and said second solvent is sulfolane, benzonitrile or nitrobenzene.

28. A process according to claim 20 further comprising (a) extracting aminophosphonium catalyst from said aqueous extract with a first organic solvent, (b) replacing said first organic solvent with a second solvent which is an aprotic solvent having a higher boiling temperature than said first solvent to form a catalyst solution, and (c) recycling at least a portion of the catalyst solution to a halogen exchange reaction.

29. A process according to claim 28 wherein said first organic solvent is methylene chloride and said second solvent is benzonitrile or nitrobenzene.

30. A halogen exchange process which comprises:
A) heating a mixture formed from ingredients comprising (i) at least one finely-divided alkali metal fluoride, (ii) at least one haloaromatic compound having at least one halogen atom of atomic number greater than 9 on an aromatic ring, (iii) an aminophosphonium catalyst, and (iv) at least one liquid aprotic solvent/diluent at one or more reaction temperatures at which at least one said halogen atom of said haloaromatic compound is replaced by a fluorine atom to thereby form (a) a vapor phase comprising at least one fluorinated aromatic compound, and (b) a residual reaction mixture comprising (i) a solids phase of alkali metal halide solids, and (ii) a liquid phase comprising aprotic solvent/diluent, aminophosphonium catalyst residue(s), and heavy ends;
B) recovering said vapor phase;
C) removing from the residual reaction mixture in any sequence, said solids and at least a portion of said aprotic solvent/diluent to leave a catalyst residue(s)-enriched mixture composed predominately of aminophosphonium catalystresidue(s) and heavy ends;
D) extracting catalyst residue(s)-enriched mixture from C) with a neutral or acidic aqueous extraction solvent medium to separate aminophosphonium catalyst residue(s) therefrom as an aqueous extract; and
E) separating aminophosphonium catalyst from the aqueous extract.

31. A process according to claim 30:
wherein in A):
said alkali metal fluoride consists essentially of potassium fluoride; said at least one haloaromatic compound having at least one halogen atom of atomic number greater than 9 on an aromatic ring consists essentially of at least one perhaloaromatic compound of the formula $C_6Cl_nBr_mF_p$ where n is from 0 to 6, m is from 0 to 6 and p is from 0 to 5, and where the sum of n, m and p is 6; said aminophosphonium catalyst consists essentially of tetra(diethylamino) phosphonium bromide or tetra(diethylamino) phosphonium chloride, or both; and said at least one liquid aprotic solvent/diluent consists essentially of (i) benzonitrile, (ii) at least one ring-substituted alkylbenzonitrile that exists as a liquid at 20° C. and 760 mm Hg pressure, (iii) nitrobenzene, (iv) at least one ring-substituted alkylmononitrobenzene that exists as a liquid at 20° C. and 760 mm Hg pressure, or (v) a mixture of any two or more of (i), (ii), (iii), and (iv);
wherein in D):
said extraction solvent medium consists essentially of water, or dilute aqueous HCl, or dilute aqueous HBr; and wherein in E):
the aminophosphonium catalyst is separated from the aqueous extract by (i) boiling off the aqueous medium from said aqueous extract and/or (ii) extracting said aqueous extract with an organic solvent.

32. A process according to claim 31 wherein in E) the aminophosphonium catalyst is separated from the aqueous extract by boiling off the aqueous medium from said aqueous extract such that an anhydrous or substantially anhydrous catalyst is formed; and wherein at least a portion of said catalyst is employed as a catalyst ingredient in another halogen exchange reaction.

33. A process according to claim 31 wherein the in E) the aminophosphonium catalyst is separated from the aqueous extract by extracting said extract with an organic aprotic solvent to form a solution of aminophosphonium catalyst in said organic solvent; and wherein at least a portion of said solution of aminophosphonium catalyst is employed as a portion of the feed to another halogen exchange reaction.

34. A process according to claim 31 wherein the organic aprotic solvent used in E) consists essentially of (i) benzonitrile, (ii) at least one ring-substituted alkylbenzonitrile that exists as a liquid at 20° C. and 760 mm Hg pressure, (iii) nitrobenzene, (iv) at least one ring-substituted alkylmononitrobenzene that exists as a liquid at 20° C. and 760 mm Hg pressure, or (v) a mixture of any two or more of (i), (ii), (iii), and (iv).

35. A process according to claim 31 wherein the in E) the aminophosphonium catalyst is separated from the aqueous extract by extracting said extract with a first organic solvent and then replacing said first organic solvent with a second solvent which is an aprotic solvent having a higher boiling temperature than said first solvent, to form a solution of aminophosphonium catalyst in said second solvent; and wherein at least a portion of said solution of aminophosphonium catalyst is employed as a portion of the feed to another halogen exchange reaction.

36. A process according to claim 35 wherein the first organic solvent used in E) consists essentially of methylene chloride and wherein the second solvent used in E) consists essentially of (i) benzonitrile, (ii) at least one ring-substituted alkylbenzonitrile that exists as a liquid at 20° C. and 760 mm Hg pressure, (iii) nitrobenzene, (iv) at least one ring-substituted alkylmononitrobenzene that exists as a liquid at 20° C. and 760 mm Hg pressure, or (v) a mixture of any two or more of (i), (ii), (iii), and (iv).

* * * * *